(12) United States Patent
Haskell et al.

(10) Patent No.: US 8,121,860 B2
(45) Date of Patent: Feb. 21, 2012

(54) PATIENT CARE AND TREATMENT DATA STRUCTURE AND PROCESSING SYSTEM

(75) Inventors: Robert Emmons Haskell, Chester Springs, PA (US); Rebecca Rae DaDamio, Sinking Spring, PA (US); Carmela Anne Couderc, West Chester, PA (US); Susan Annette Matney, Woods Cross, UT (US); Mary Ellen Dlugos, King of Prussia, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 357 days.

(21) Appl. No.: 12/433,552

(22) Filed: Apr. 30, 2009

(65) Prior Publication Data

US 2009/0276241 A1    Nov. 5, 2009

Related U.S. Application Data

(60) Provisional application No. 61/049,470, filed on May 1, 2008.

(51) Int. Cl.
    *G06Q 10/00*    (2012.01)
    *G06Q 50/00*    (2012.01)
(52) U.S. Cl. .................. 705/2; 705/3; 707/705
(58) Field of Classification Search ............... 705/2–3; 707/100, 705; 600/300
    See application file for complete search history.

(56) References Cited

U.S. PATENT DOCUMENTS

| | | | |
|---|---|---|---|
| 6,272,481 B1 | 8/2001 | Lawrence et al. | |
| 6,401,072 B1 | 6/2002 | Haudenschild et al. | |
| 7,747,392 B2* | 6/2010 | Ruano et al. | 702/19 |
| 7,925,603 B1* | 4/2011 | Laidig et al. | 706/45 |
| 2006/0167721 A1 | 7/2006 | Bernard et al. | |
| 2007/0244723 A1 | 10/2007 | Nagaeda | |
| 2008/0086336 A1 | 4/2008 | Hertel et al. | |
| 2010/0324925 A1* | 12/2010 | Barkan et al. | 705/2 |

OTHER PUBLICATIONS

The International Organization for Standardization, Health Informatics—Integration of a reference terminology model for nursing (ISO 18104:2003); German version EN ISO 18104:2003, text in English. International Classification of Nursing Practice, ICNP Version 1.0 Book, Chapter 2—INCP Development, 2005, place Jean-Marteau, 1201 Geneva (Switzerland).

* cited by examiner

*Primary Examiner* — Luke Gilligan
(74) *Attorney, Agent, or Firm* — Alexander J Burke

(57) ABSTRACT

An expected outcome data system stores data representing a plurality of different expected outcomes of patient care and treatment for use in providing healthcare to a patient. An acquisition processor acquires data representing an expected outcome of treatment associated with a medical problem for storage in a repository. A repository, electrically coupled to the acquisition processor, includes data representing a plurality of different expected outcomes; an individual expected outcome has an expected outcome name and is characterized by expected outcome attributes; an individual expected outcome has a plurality of attribute properties determining how an expected outcome attribute is represented. Expected outcome attributes include a focus term indicating a topic of an expected outcome, an expected outcome likelihood term indicating an assessment of likelihood of the associated corresponding expected outcome, and a client term indicating at least one target person for care. The attribute properties include a format attribute property indicating a format constraint of an expected outcome attribute and a content attribute property indicating a content constraint of an expected outcome attribute. A retrieval processor, electrically coupled to the repository, retrieves data representing at least one expected outcome from the repository.

25 Claims, 14 Drawing Sheets

ID

PATIENT CARE AND TREATMENT DATA STRUCTURE AND PROCESSING SYSTEM

This is a nonprovisional patent application that claims priority from U.S. Provisional Patent Application Ser. No. 61/049,470 filed on May 1, 2008 by Robert Haskell et al.

FIELD OF THE INVENTION

The invention concerns a standardized patient care and treatment data structure and processing system for use in providing healthcare to a patient population.

BACKGROUND OF THE INVENTION

In the healthcare industry there are multiple clinical terminologies in use. Each different set of clinical terms are associated with their own set of pre-coordinated, free text patient expected outcomes. These sets of patient expected outcomes are further associated with their own either implicit or explicit terminology models. A problem arises when different participants in the healthcare industry want to communicate with one another. For example, the free text expected outcome in one healthcare system can neither be understood nor mapped for use by a second different healthcare system in any objective way, except through communication between expected outcome terminology developers associated with their respective healthcare system. These developers understand the meaning of their own expected outcomes. However, even then, direct equivalence is often not possible. Currently, there is a lack of a single model of patient expected outcomes that provide:

A single definition of patient expected outcomes which can be specialized to drive the behavior of any model-driven operational system, and can serve as the basis for consistent and uniform point of care data collection;

A single interlingua for use in translating a meaning of clinical terms between different participants in healthcare system. For example, known systems are unable to translate between healthcare operational systems, between healthcare operational systems and external knowledge sources and translation between terminologies used by different healthcare systems;

A single dialog definition for use in defining contextual constraints necessary to drive a clinical dialog (e.g., patient characteristics, other attribute values) affecting workflow within a healthcare system; and A single authoring definition for use in guiding and constraining authoring dialogs for users defining new patient expected outcomes.

A further deficiency in known healthcare information systems is the lack of support for model-driven definitions of patient expected outcomes, and clinical applications driven by patient expected outcome models. Existing clinical terminologies include patient expected outcomes/goals, but these expected outcomes/goals are mostly not based on underlying models. While Healthcare Information Technology (HIT) systems may use these terminologies, these systems do not utilize a model-based implementation. Therefore, while the International Council of Nurses (ICN) created the International Classification for Nursing Practice (ICNP®) Version 1 to represent clinical diagnoses (client status, problems, needs, and strengths); clinical interventions (or clinical actions); and clinical outcomes, known HIT systems are unable to efficiently use the ICNP® across a healthcare enterprise. The ICNP® describes a 7-Axis Model that facilitates the composition of these statements (diagnoses, interventions and outcomes). However, this known model of patient expected outcomes/goals is not sufficiently described to enable their use within an operational HIT system, such as an interdisciplinary plan of care application. The known industry models have insufficient specificity of detailed attributes to support application requirements and insufficient supporting attribute properties to define application and user interface behavior. Moreover, any HIF systems that do not utilize model-driven function are not able to decompose expected outcomes into a consistent, unambiguous, and computable definition, which enables secondary data use based on specific expected outcome characteristics. Simple text expression of a patient expected outcome is insufficient to support optimizing clinical practice for individual patients at the point of care, as well as managing clinical outcomes for patient behavior in the aggregate.

Thus, in known systems, data is not easily shared across systems that do not use common and semantically consistent definitions. These systems do not include standard models to help promote consistent data usage across healthcare enterprise or different enterprises. A system according to invention principles addresses these deficiencies and related problems.

BRIEF SUMMARY OF THE INVENTION

An expected outcome data system stores data representing a plurality of different expected outcomes of patient care and treatment for use in providing healthcare to a patient. An acquisition processor acquires data representing an expected outcome of treatment associated with a medical problem for storage in a repository. A repository, electrically coupled to the acquisition processor, includes data representing a plurality of different expected outcomes; an individual expected outcome has an expected outcome name and is characterized by expected outcome attributes; an individual expected outcome has a plurality of attribute properties determining how an expected outcome attribute is represented. Expected outcome attributes include a focus term indicating a topic of an expected outcome, an expected outcome likelihood term indicating an assessment of likelihood of the associated corresponding expected outcome, and a client term indicating at least one target person for care. The attribute properties include a format attribute property indicating a format constraint of an expected outcome attribute and a content attribute property indicating a content constraint of an expected outcome attribute. A retrieval processor, electrically coupled to the repository, retrieves data representing at least one expected outcome from the repository.

DETAILED DESCRIPTION OF THE INVENTION

Figure 1:
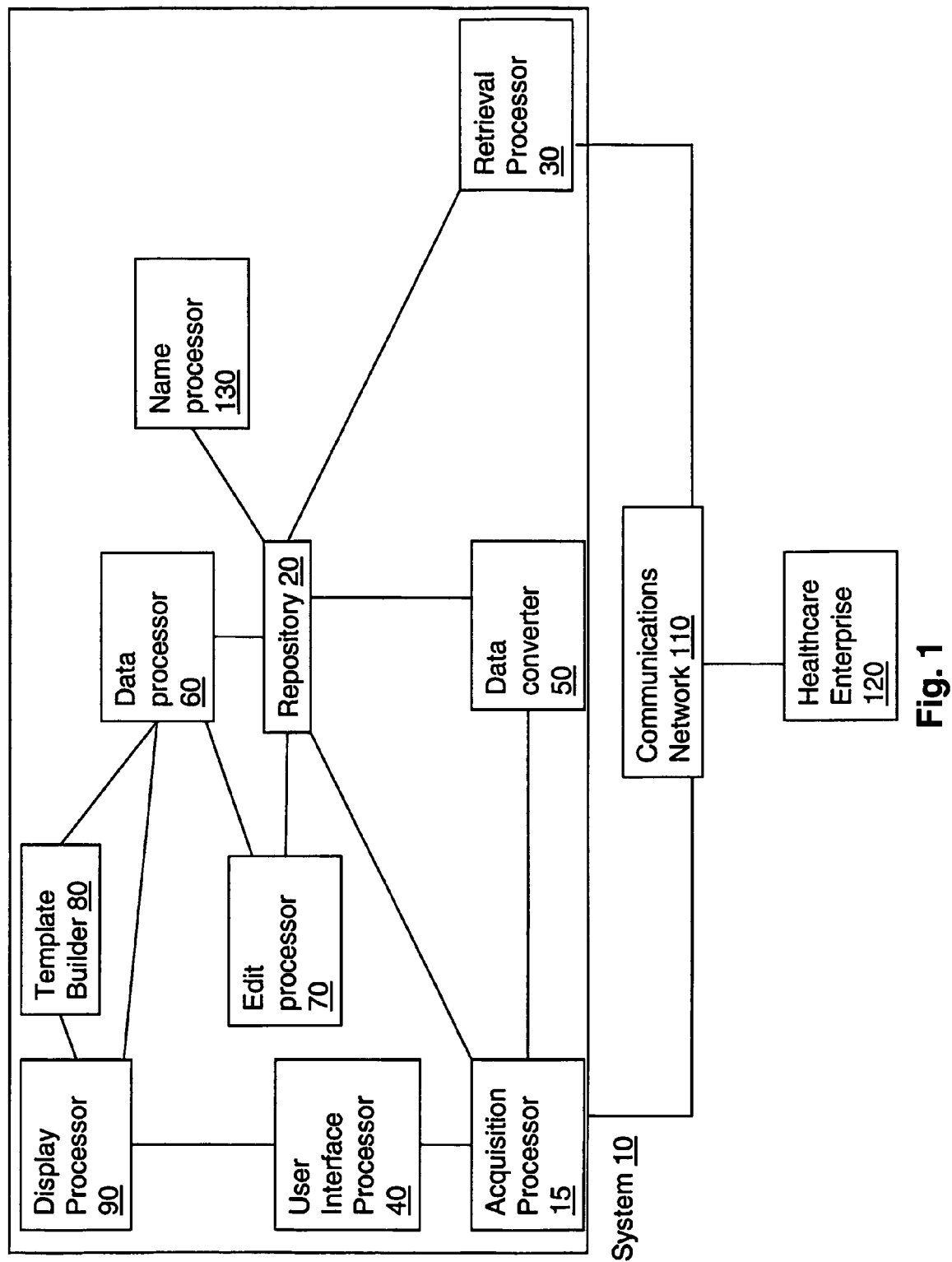
FIG. 1 is a block diagram of the system for providing a patient care and treatment data structure and processing according to invention principles.

A system, as shown in FIG. 1, according to invention principles advantageously enables consistent, model-driven application and user interface behavior associated with the collection, translation and interpretation of patient expected outcomes. An expected outcome is an objective to be achieved within a particular time frame. In this instance a patient expected outcome is an objective to be achieved by a nurse or other medical personnel within a particular time frame. The system includes a model structure including detailed attributes associated with patient expected outcomes and supplemental information associated with patient expected outcomes that is necessary to drive application behavior. The system further enables consistent data collection across applications. The system implements a model used by a clinical application and a user interface to determine data that is collected, processed, and stored for secondary use. Because a patient expected outcome meaning can be unambiguously and individually defined through the model, the data collected are semantically consistent and can be easily shared within the interdisciplinary team caring for a patient, and aggregate patient practice can be compared across clinical settings, "client" populations, geographic areas, or time periods. This model supports a total infrastructure needed to create a "knowledge-driven" plan of care and electronic medical record (EMR) for use by a healthcare enterprise system. Thus, the system further advantageously provides a common industry reference model able to decompose a patient expected outcome phrase into a consistent, unambiguous, and computable definition for operational use within a clinical HIT application. Decomposition of an expected outcome phrase is performed computationally utilizing a pre-coordinated text expected outcome for determining the expected outcome's true semantic meaning.

The expected outcome modeling system advantageously supports a care plan application implemented across a healthcare enterprise. The system provides a standard, application-independent structure (logical information model) that determines the construction and definition of individual, unambiguous, and computable patient expected outcomes. The model identifies the attributes and structure necessary to define a clinical patient expected outcome, in a form that can be used within an information system in the context of a patient. The model identifies the data attributes, their semantics within the expected outcome, and links to equivalent standard terminologies. The system further enables Model-driven application behavior utilizing model structure and attributes to define behavior of a user interface and clinical application business logic. These structures and attributes are application independent, such that multiple applications operate using a single definition within a particular record in the model. Additionally, the collection of standardized and structured data of a patient expected outcome enables a hospital information system to manage the operation of individual healthcare applications, for example, rule and workflow applications, reporting and analysis of patient data, and regulatory compliance. Thus, the patient expected outcome system facilitates interoperability across multiple platforms and applications within a hospital information system. Interoperability is further affected by utilizing patient expected outcome models for migrating versions of individual healthcare applications or migrating data to a second different application. By externalizing the definition of clinical objectives to be achieved by healthcare personnel into a standard model, the underlying clinical applications can be migrated with minimal effort. Using model specific data structures enables integration of individual clinical systems by driving application behavior and data collection promotes collaborative systems and improved interoperability.

Expected Outcome Data System 10 (FIG. 1) provides a model data structure that uses detailed attributes within each individual model, to facilitate consistent data collection, storage, and processing of patient expected outcome phrases. The model identifies attributes that define a clinical patient expected outcome in a form that can be used within any information system. The attributes are collected and standardized to advantageously allow System 10 to provide a model that can be used in multiple different clinical applications. One particular set of attribute properties needs to exist for each clinical application. As a result, System 10 provides a standardized universal model that is the same across clinical applications, yet provides the flexibility for the use of the model to differ between each clinical application. The model-driven functionality of Expected Outcome Data System 10 automatically decomposes expected outcomes into consistent, unambiguous, and computable definitions that facilitate efficient and consistent data sharing across a multitude of information systems, throughout and between different healthcare enterprises.

A block diagram for a system for storing and processing data structures related to patient care is shown in FIG. 1. An executable application, as used herein, comprises code or machine readable instructions for conditioning a processor to implement predetermined functions, such as those of an operating system, a context acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

A user interface (UI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application manipulates the UI display images in response to the signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure. A document or record comprises a compilation of data in electronic or paper form.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams. A document or record comprises a compilation of data in electronic form and is the equivalent of a paper document and may comprise a single, self-contained unit of information.

A repository 20 stores data including data representing a plurality of different expected outcomes. An expected outcome is defined as a clinical objective that is to be achieved within a given time period. The objective may be measured subjectively through a judgment (e.g., Effective Gas Exchange), or objectively through a result, (e.g., Decreased Pain). Each individual expected outcome has an expected outcome name that is characterized by expected outcome attributes. An expected outcome name is a clinical statement, such as Effective Gas Exchange, that is defined by the individual combination of associated expected outcome attribute values. As a result, an individual expected outcome name may be standardized to be consistently constructed with a given set of expected outcome attributes. The expected outcome attributes consist of a focus term to describe the topic of attention, a likelihood term to describe the probability of the topic of attention, a client term to describe the target of care, and a judgment term to describe the clinical opinion or determination about the actual or potential health problem, which are described below in connection with FIGS. 5A-5F. The judgment term may indicate a positive state (e.g., increase), negative (e.g., impairment), or neutral state (e.g., not valued). The judgment term is typically the first word in an expected outcome name, except when certain exceptions occur, as described below and shown in FIGS. 5A-5F. Additional expected outcome attributes which may be utilized are: (a) time (which is derived from one or more of the following attributes: condition acuity, chronologic developmental stage, start evaluation time, time pattern), (b) severity, and (c) location. These additional expected outcome attributes are described below and shown in FIG. 6. The expected outcome attributes may also include an indication of review action and an indication of approval action needed in the treatment of a medical condition.

Expected outcome attributes are characterized by attribute properties which determine how an expected outcome attribute is represented or used in conjunction with a particular clinical application. An individual application in communication with system 10 uses its own individual attribute properties to account for behavior differences and constraints within a particular clinical application's user interface characteristics. Attribute properties include a format attribute property, a content attribute property, and a processing attribute property. Format attribute property indicates a format constraint of an expected outcome attribute which dictates how a particular expected outcome attribute is formatted or presented. Format constraints include at least one of: (a) maximum character length of an attribute, (b) unit of measure of an attribute, and (c) number of decimal places an attribute has. Format constraints may have default values that are selectively assignable by a user. Content attribute property indicates a content constraint of an expected outcome attribute, which dictates how a particular expected outcome attribute may be modified. Content constraints include at least two of: (a) an allowable value set of an attribute, (b) a default value of an attribute, (c) a maximum number of values allowed for an attribute, and (d) an indication that free text entry is allowable for user entry of data representing an attribute. Processing attributes are parameters which provide information on how a particular outcome attribute is to be edited, used, or displayed. Processing attributes are composed of properties including at least one of: (a) an indication an attribute is to be processed in performing a check for a duplicate expected outcome, (b) an indication a default value is required for an attribute, (c) an indication an attribute is required for use by an executable clinical application, (d) an indication an attribute is displayed in a display image associated with an executable clinical application, and (e) an indication an attribute value may be overridden.

Repository 20 further includes metadata attributes associated with a particular patient expected outcome. Metadata attributes include at least one of: (a) an expected outcome, (b)

external references, (c) synonyms, and (d) data identifying who created, changed, or reviewed expected outcome information, which are associated with an individual expected outcome. Metadata attributes are defined as common concepts in the patient expected outcome model and further define an expected outcome attribute. These attributes contain administrative and supplemental information to further describe the model.

System 10 also includes an acquisition processor 15, electrically coupled to repository 20 and communications network 110. Processor 15 is conditioned for acquiring data representing an expected outcome of treatment associated with a medical problem for storage in repository 20. Acquired data is derived from repository 20 or from a remote system in a healthcare enterprise 120 via a communications network 110. Acquired data, in one embodiment, is acquired automatically from a source in response to an initiated executable procedure, an attribute property driving operation of individual application, or in response to user input. Acquisition processor 15 is conditioned in response to executable instruction to load system 10 with model-based expected outcomes for use in clinical applications, as well as ensure that the loaded expected outcomes are compatible with attribute properties for use with those clinical applications. Acquisition processor 15 further acquires data representing an expected outcome compatible with particular attribute properties for storage in repository 20.

System 10 further includes retrieval processor 30 electrically coupled to repository 20 and communications network 110 in order to retrieve data representing at least one expected outcome from repository 20. Retrieved data may be transmitted for receipt by communications network 110. Acquisition processor 15 and retrieval processor 30 are electrically coupled to communications network 110 to facilitate communication and data transmission between the system 10 and healthcare enterprise 120. Healthcare enterprise 120 includes any system within a healthcare information system, for example clinical information system, workflow system, financial information system. Healthcare enterprise 120 may include systems that are commonly operated by a single healthcare entity or systems operated by distinctly owned and operating healthcare providers. Data representing an expected outcome is bidirectionally communicated between system 10 and enterprise 120. Communication occurs in any of following instances: (a) when an expected outcome is loaded into system 10, or (b) in response to population of attributes of patient expected outcome model for a particular expected outcome.

System 10 includes data converter 50 electrically coupled to repository 20 and acquisition processor 15. Data converter 50 converts data representing an expected outcome acquired by acquisition processor 15, automatically or in response to user command, to be compatible with attribute properties stored in repository 20 or attribute properties of a particular clinical application. Data converter 50 facilitates interoperability between different information systems within a healthcare enterprise by providing a common data syntax of attributes that are used by system 10 for translating patient expected outcomes into a common format and for driving application operation based on the expected outcome data.

User interface processor 40 is electrically coupled to acquisition processor 15 and is conditioned to provide data representing at least one display image including image elements that allow a user to enter expected outcome attributes, as well as prompt a user to select corresponding attribute properties. In response to loading of data representing an expected outcome, expected outcome data is computationally decomposed into expected outcome attributes. These attributes are matched to attributes of an already defined expected outcome. If the attributes do not match, a new expected outcome is added. User interface processor 40 facilitates the addition of a new expected outcome by allowing a user to specify attribute properties for already entered expected outcome attributes, or further define an expected outcome by entering additional expected outcome attributes and define their corresponding attribute properties. In addition, user interface processor 40 enables a user to visually organize similar expected outcomes to create a set of expected outcomes by providing a display image including user selectable image elements for selecting a plurality of expected outcome data instances for inclusion as a set of expected outcomes. Expected outcome set creation is further described with respect to FIG. 6.

Edit processor 70 facilitates efficient changes to data representing expected outcomes. Edit processor 70, electrically coupled to repository 20 and data processor 60, allows a user to edit data representing an expected outcome of treatment associated with a medical problem for storage in repository 20. In certain circumstances, attribute values of expected outcomes are changed to either create an entirely new expected outcome, or alternatively edit the existing expected outcome. When expected outcome attributes are modified, added, or deleted, the expected outcome name may change, which results in an entirely new expected outcome to be added to repository 20. In addition, edit processor 70 facilitates the modification of attribute properties to conform an expected outcome to attribute properties specific to particular clinical applications.

System 10 further enables a user to generate data representing an expected outcome via template builder processor 80. Template builder processor 80 is electrically coupled to display processor 90 and data processor 60 and allows a user to generate data representing an individual expected outcome or an expected outcome set comprised of a plurality of individual expected outcomes. Template builder processor 80 facilitates the changing of expected outcome attributes and attribute properties in order to create or modify expected outcomes. Template processor 80 operates under direction of stored executable instructions and provides data to display processor 90 representing a display image including at least one user selectable image element enabling a user, via a user interface, to selectively modify expected outcome data by adding, deleting or changing at least one of attributes and attribute properties associated with at least one expected outcome or set of expected outcomes.

Data processor 60 is electrically coupled to repository 20, display processor 90, edit processor 70, and template builder processor 80, searches data in repository 20 to identify a particular expected outcome in response to user entered data representing outcome attributes and/or attribute properties. Data processor 60 searches repository 20 to identify at least one of: (a) a candidate plan of care, (b) a treatment, and (c) a diagnosis, associated with a particular expected outcome in response to user entered data identifying expected outcome attributes having certain attribute properties. In response to loading by system 10 of expected outcome data, system 10 automatically decomposes expected outcome attributes in order to match attributes with expected outcome attributes of expected outcomes already stored in repository. Expected outcome data includes at least one attribute data field and the at least one attribute data field includes at least one attribute property data field corresponding to a term of the expected outcome data. Additionally, as will be discussed with respect to FIGS. 5A-5F, data processor 60 analyzes the order of terms comprising expected outcome data to determine if expected outcome data already exists on system 10. Attribute data fields and attribute property data fields include different data values corresponding to characteristics that define expected outcome data. Data processor 60 automatically decomposes expected outcome data by parsing acquired expected outcome data to determine a number of attribute data fields and attribute property data fields associated with the identified attribute data fields. Data processor 60 uses data values in attribute fields and attribute property fields and compares the identified data values with attribute data values and/or attribute property data values associated with the particular expected outcome model and which are stored in repository 20. Data processor 60 automatically determines if attributes match in order to ascertain that an expected outcome is a duplicate and does not need to be added to repository 20 thereby facilitating a consistent model for use by any clinical application or driving operation of a clinical application within a healthcare system.

System 10 includes name processor 130 electrically coupled to repository 20, for automatically allocating a name to an expected outcome in response to predetermined naming rules. An expected outcome name is generated by name processor 130 based upon expected outcome attributes, for example using terms stored in any of judgment attribute, client attribute, focus attribute, and likelihood attributes. The predetermined naming rules used in this case is described below and shown in FIGS. 5A-5F.

Figure 2:
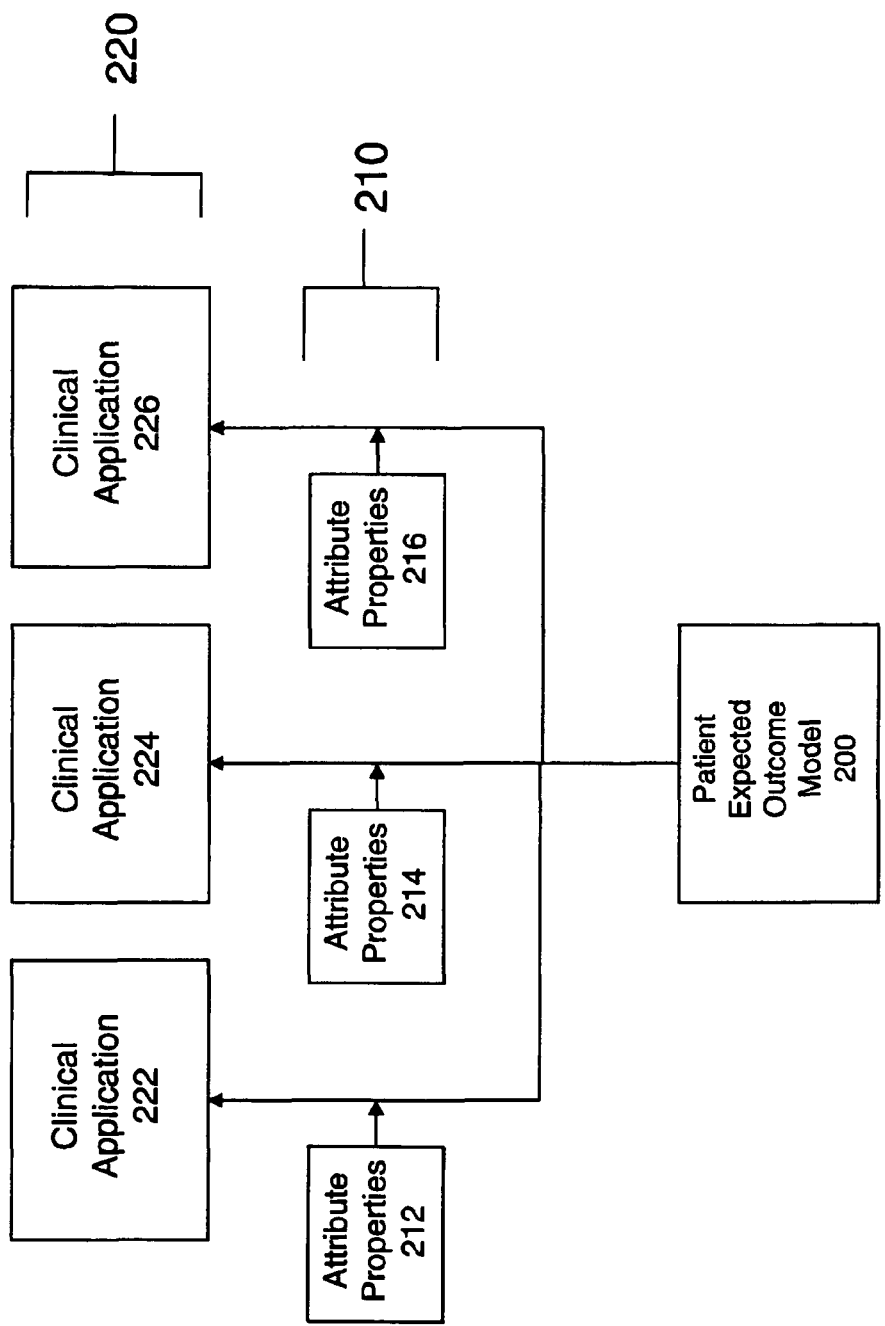
FIG. 2 is a block diagram showing a patient expected outcome model and its interaction with a plurality of clinical applications according to invention principles.

A block diagram showing a patient expected outcome model and its interaction with a plurality of clinical applications is shown in FIG. 2. Patient Expected Outcome Model 200 is the common patient expected outcome model stored in repository 20 of system 10. Patient Expected Outcome Model 200 is used by a plurality of clinical applications 220. For example, clinical application 222 may be a radiology information system that uses data in model 200 for assigning a task to a particular worker to obtain an image study for a particular patient based on expected outcome data. While FIG. 2 illustrates three clinical applications 222, 224 and 226, any number of clinical or other applications that operate in a healthcare enterprise may be in communication with system 10 and able to use model 200 for presenting patient data in a desired manner or causing an application to operate in a specified manner. Model 200 includes data representing patient expected outcome and attribute properties associated with particular patient expected outcome data. Attribute properties 210 are application specific attributes that specify how attributes within Patient Expected Outcome Model 200 are used by a particular clinical application. For example, a specific set of attribute properties 212 exist for clinical application 222. Clinical applications parse expected outcome data to determine data values of attribute properties. The data values of attribute properties provide operating instructions to a respective clinical application driving operation of the clinical application or determining the manner in which the clinical application uses the patient expected outcome data. Thus, since attribute properties 212 and 214 will differ since they correspond to clinical application 222 and 224 respectively, the use of Model 200 within clinical application 222 and 224 will likewise differ. As a result, specific attribute properties are available for each expected outcome attribute for a particular clinical application to drive the application and determine user interface behavior. System 10 advantageously provides a repository of patient expected outcomes that is selectively modifiable and expandable to enable a user to easily set attribute properties associated with a particular patient expected outcome and which are useable by a plurality of different applications in a healthcare system.

Figure 3:
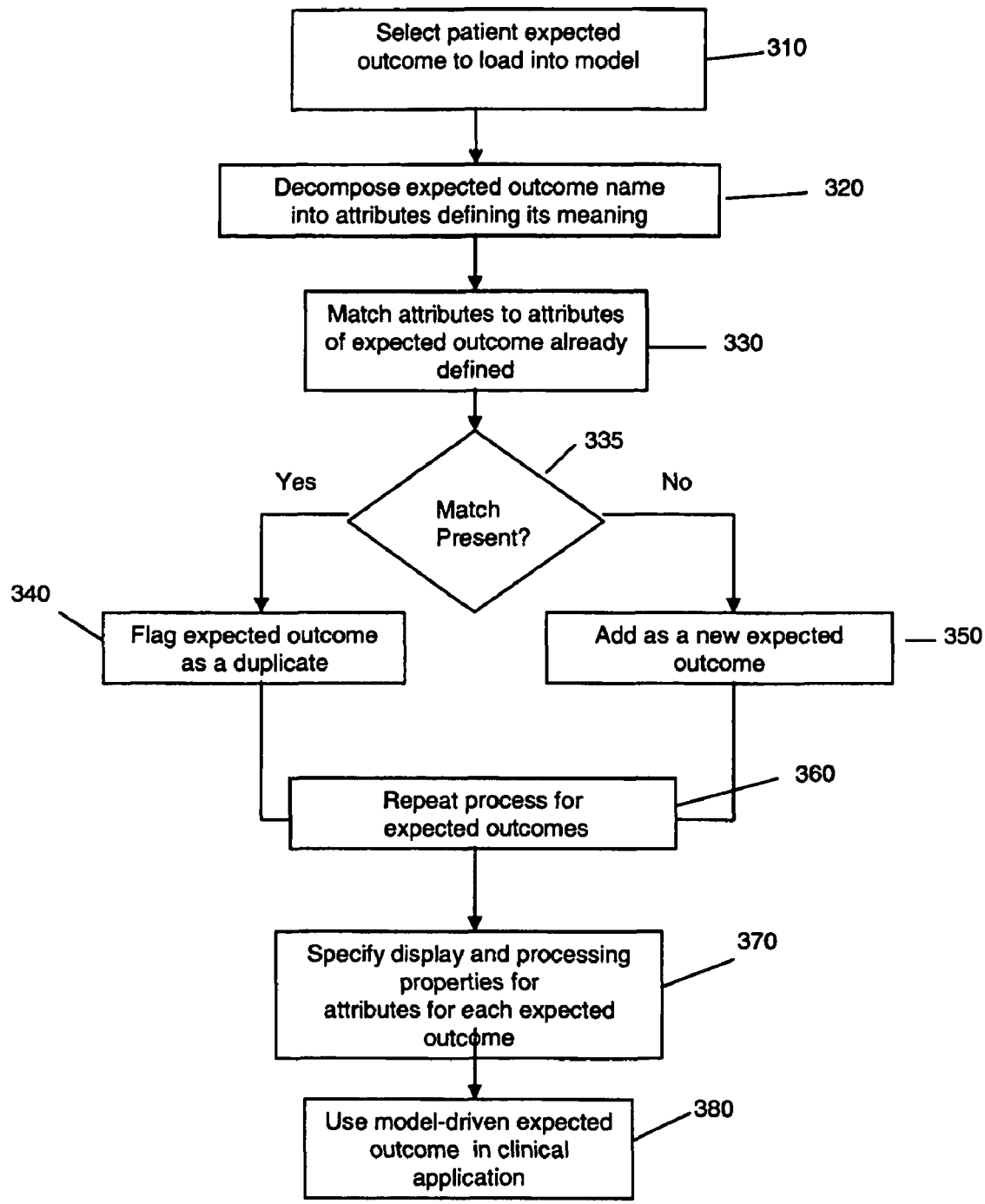
FIG. 3 is a flow diagram showing the usage of the system for loading a model based set of patient expected outcomes for use in a clinical application according to invention principles.

A flow diagram detailing the use of system 10 for loading a model based set of patient expected outcomes for use in a clinical application is shown in FIG. 3. In Step 310, a patient expected outcome is loaded into a model stored in repository 20 of system 10. In response to loading a model, in step 312, system 10 automatically decomposes, in the manner discussed above with respect to FIG. 1, an expected outcome name associated with a particular patient expected outcome into corresponding expected outcome attributes which define the meaning of the expected outcome name. These expected outcome attributes are the judgment, client, focus, and likelihood terms. In step 330, system 10 matches the decomposed expected outcome attributes to the expected outcome attributes of previously defined expected outcomes which are stored in repository 20 of system 10 by comparing data values in attribute data fields and attribute property data fields with data values stored in repository 20 and which correspond to previously defined expected outcome data. Step 335 queries whether or not a match is present during the comparison made in step 330. If the expected outcome attributes match, then the received expected outcome is flagged as a duplicate in step 340 and system operation continues at step 360. In the event that the expected outcome attributes of the decomposed expected outcome name do not match with attributes of already stored and defined expected outcomes, system 10 automatically adds a record comprising a previously un-entered expected outcome name and any associated attributes in step 350. The system operation continues at step 360 wherein system 10 repeats the operation detailed in steps 310-350 for the remaining expected outcome names loaded into system 10. When the process is complete for expected outcomes in step 360, step 370 allows a user or System 10 to specify attribute properties that correspond to the expected outcome attributes for each expected outcome. Upon completion of step 370 for loaded expected outcomes, step 380 indicates that the model-driven expected outcome set is ready for use in a particular clinical application.

Figure 4:
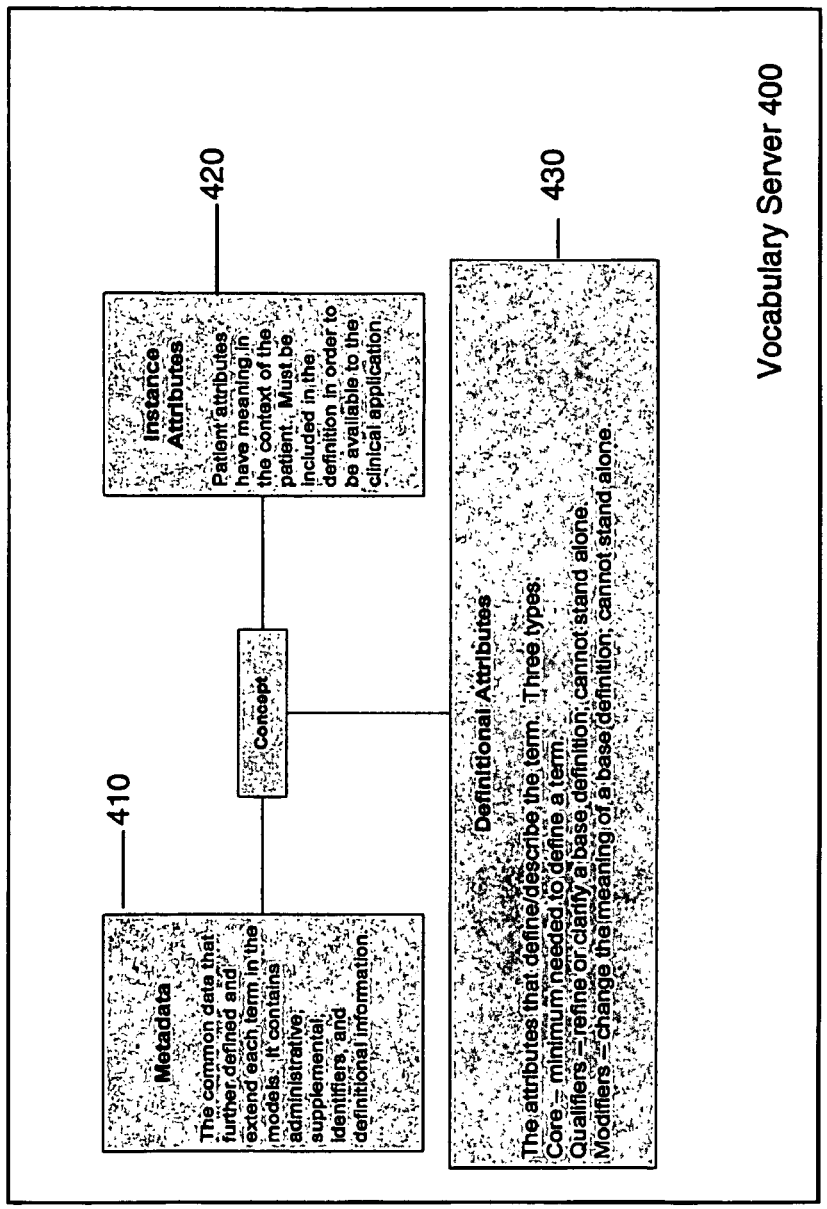
FIG. 4 is a block diagram detailing the setup and interaction of metadata and attributes within the model according to invention principles.

The structure of an exemplary patient expected outcome concept is shown in FIG. 4. An individual patient expected outcome concept is created using a vocabulary server 400 which defines key attribute values and properties that describe a respective expected patient outcome. The concept and supporting structure, referred to as a definition instance, are created and stored in vocabulary server 400. A particular concept may be defined as the medical problem as a whole, including associated attributes and attribute properties. A clinical application, for example a patient record updating system, searches for and uses a definition instance in the creation of a patient instance associated with the patient expected outcome. The patient instance is defined by the definition instance and includes additional attribute values and properties that are applicable to describe a patient outcome. A clinical application facilitates storage of the patient instance in patient record of the particular patient.

Attributes, as shown in FIG. 4, include metadata 410, instance attributes 420, and definitional attributes 430. Attributes of an expected outcome model direct operation of the clinical application, in this case the patient record update system, and corresponding user interface presented to an operator of the clinical application. Since an individual clinical application uses a common patient expected outcome model provided by system 10, an individual clinical application is provided with a standard and consistent set of definitions from central vocabulary server 400. Attributes also include attribute properties which are data values associated with respective patient expected outcomes that provide data describing desired application behavior associated with a specific attribute. Generally, these properties exist to serve the purpose of business logic control (e.g., duplicate checking) or user interface (e.g., display in a clinical application).

Patient instance attributes 420 and definitional attributes 430 are included in the models to support data-driven applications. Definitional attributes 430 describe an expected outcome independent of the context in which they may be used. Definitional attributes are further divided into core attributes, qualifiers, and modifiers. Core attributes are required attributes define a concept within an expected patient outcome and are part of a pre-coordinated term. Qualifiers act to refine or clarify a base definition represented by core or other definitional attributes, such as severity, location, and time. Qualifiers may be single or multiple definitional attributes, as well as a pre-coordinated concept. Qualifiers terms are not required and do not function without the core attributes. Modifiers may change the meaning of a base definition, but also do not function without the core attributes.

Patient instance attributes have meaning in relation to, and in the context of, a specific patient. The specific purpose of patient instance attributes is to direct operation of the user interface, which is the point where data is collected. Patient instance attributes also include allowable value sets and characteristics of definitional attributes which serve to direct application operation and corresponding user interface.

Metadata attributes are common data which further define and extend the concepts, or expected outcomes, in the models. Each expected outcome, expected outcome attribute, and expected outcome attribute property is created as an individual concept within the general vocabulary server. Metadata may contain administrative, supplemental, identifier, and definitional information. Administrative information includes the source, version, status, creation date/time, create user id, change data/time, change user id, review date/time, review user id, review comment, approval date/time, approval user id, and approval comment. Supplemental information includes a synonym or external reference value that correlates with at least one other element of expected outcome data. Definitional information includes a concept type identifier, concept name, description, and text/text type. Metadata attributes advantageously enable system expansion to allow later deployed clinical applications to interface with system 10 and utilize the model of patient expected outcome to facilitate patient specific data collection and/or workflow modification of a healthcare worker tasked with providing a healthcare service to the particular patient using the application.

System 10 is able to create and/or decompose patient expected outcome data. Patient expected outcome data includes data representing patient expected outcome names. Patient expected outcome name data includes a plurality of descriptor fields that are used to provide a common consistent set of definitional terms usable by multiple systems in a healthcare enterprise. Expected outcome name data is generated by imbedding data in descriptor attribute data fields in a particular sequence. Exemplary data structures for expected outcome name data is shown in FIGS. 5A-5F. A pre-coordinated expected outcome is a patient expected outcome statement, for example, Effective Gas Exchange. The individual meaning of the statement is defined by a unique combination of associated attribute values defined in particular fields. An individual expected outcome statement name may be construed consistently using rules or attributes that allow the name to be composed in a specific sequence.

Figure 5A:
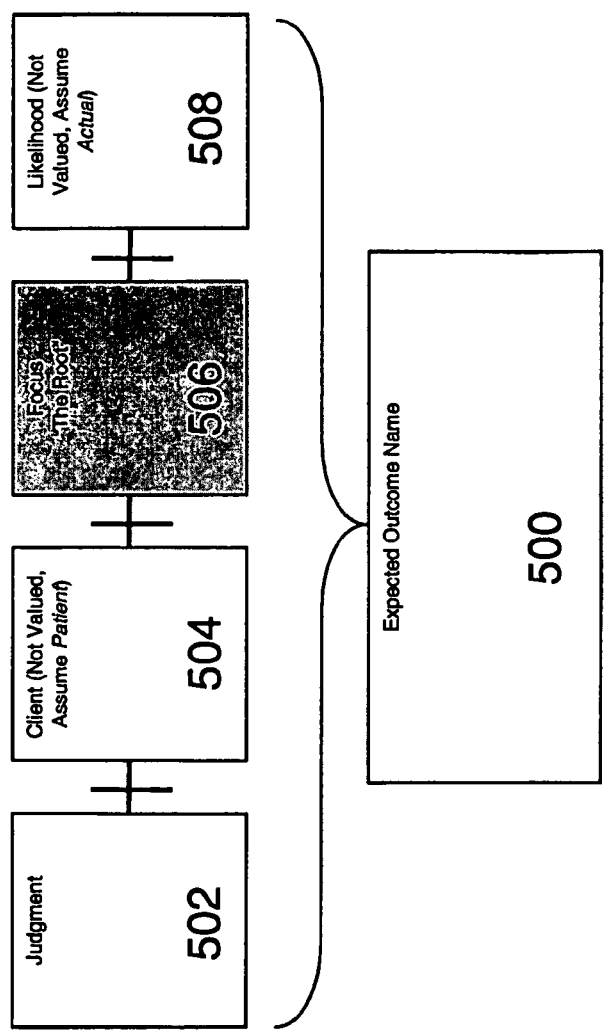
FIGS. 5A-5F show the structure of an expected outcome name according to invention principles.

FIG. 5A shows an exemplary structure of an expected outcome name 500 and its associated attribute terms in respective data fields 502-508. Attribute data fields associated with an expected outcome name include a judgment field 502, client field 504, focus field 506 and likelihood field 508. A data value in the judgment field 502 is a term identifying a judgment associated with an expected outcome or a synonym for judgment term. The judgment term is the first word in the expected outcome name 500, except in certain circumstances which are discussed below. For example, an adjective describing an action, such as "diminished", is set as the value of judgment term 502 in expected outcome name 500. Focus term 506 is characterized as "the root," which is included in the expected outcome name 500. The value set in the Focus term field 506 is associated with a medical problem affecting a patient. Once set, the value of the focus term field 506 is automatically included in the resulting expected outcome name 500 following the value of judgment term field 502. Likelihood term field 508 includes a value set to indicate an assessment of likelihood of the associated corresponding expected outcome, for example "Risk". Structurally, the value in likelihood term field 508 follows both judgment term 502 and focus term 506 in the resulting expected outcome name 500. Additionally, expected outcome name 500 may include a further value derived from client term field 504. The value in client term field 504 defines a person to which expected outcome name 500 is associated. Typically the value in client term field 504 is set to "patient," in which case client term 504 will not appear in expected outcome name 500. Cases where client term 504 has a value other than "patient" are included in expected outcome name 500. An example of this instance is discussed below in FIG. 5E.

Figure 5B:
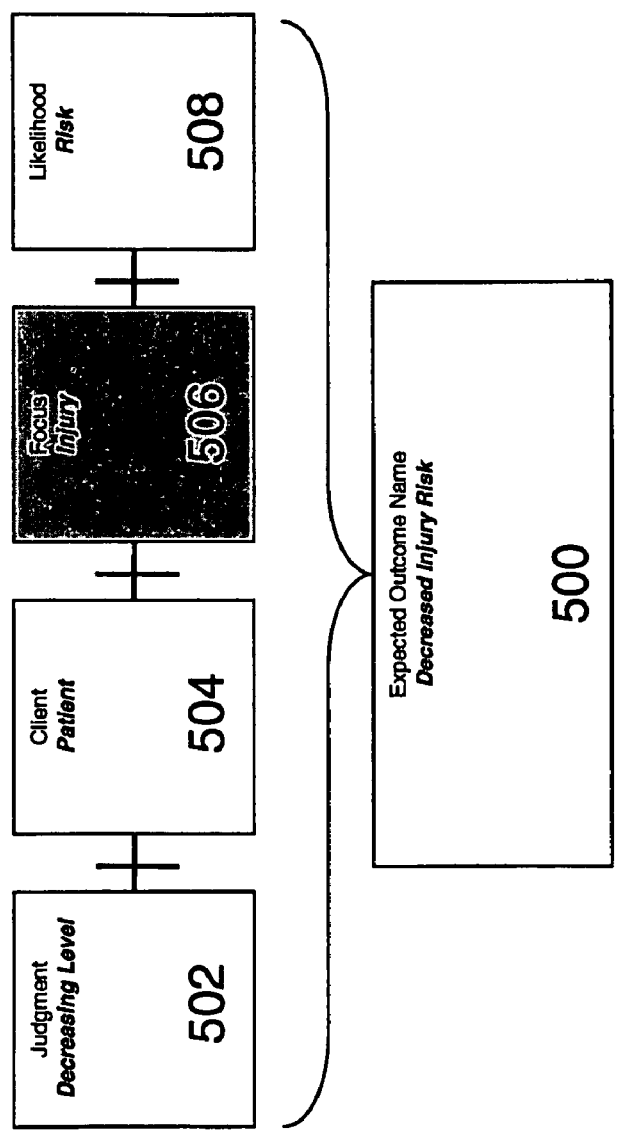

FIG. 5B is an exemplary structure of expected outcome name 500 defined as "Decreased Injury Risk". Expected outcome name 500 in FIG. 5B is generated from data set in attribute fields 502-508. The values of attribute fields 502-508 are set as follows: (a) judgment field 502 is set to "Decreased Level"; (b) client field 504 is set to "Patient", (c) focus field 506 is set to "Injury"; and (d) likelihood field 506 is set to "Risk". The resulting expected outcome name is derived from fields 502-508 as discussed above and is able to be processed by system 10 as "Decreased Injury Risk". In this example, the value of the likelihood field is different than the term "actual" and thus appears in the resulting expected outcome name 500. Additionally, as the value in client field 504 is set to "Patient", this value does not appear in the resulting expected outcome name.

Figure 5C:
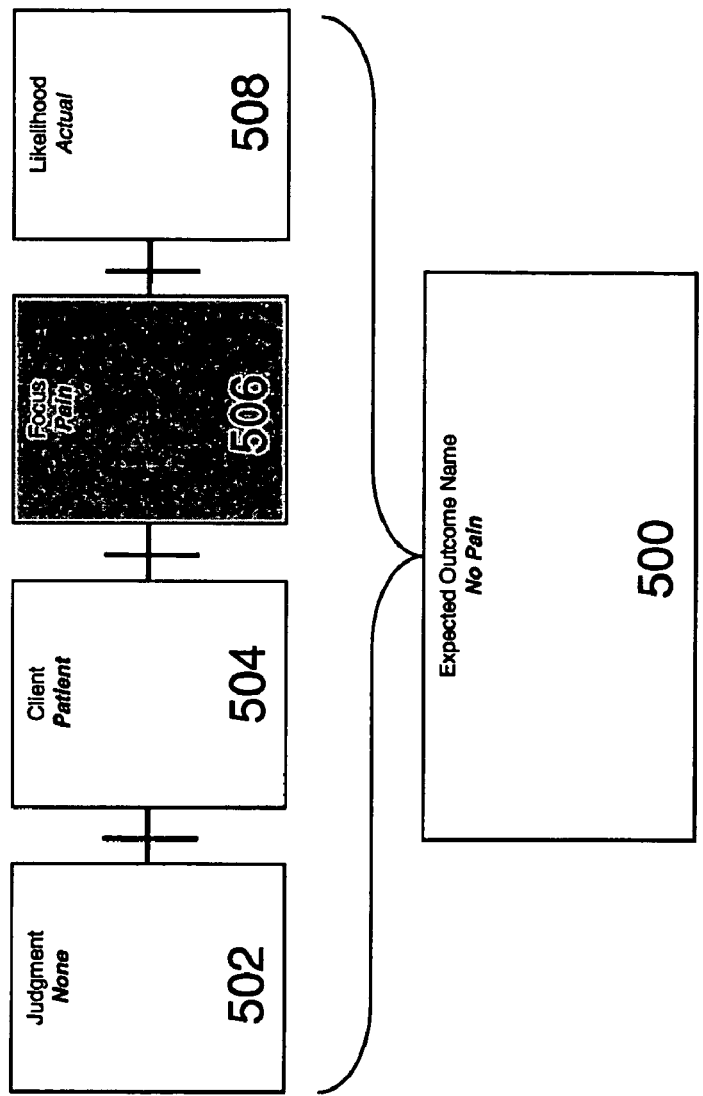

FIG. 5C is an exemplary structure of expected outcome name 500 defined as "No Pain". Expected outcome name 500 in FIG. 5B is generated from data set in attribute fields 502-508. The values of attribute fields 502-508 are set as follows: (a) judgment field 502 is set to "None"; (b) client field 504 is set to "Patient", (c) focus field 506 is set to "Pain"; and (d) likelihood field 506 is set to "Actual". The resulting expected outcome name is derived from fields 502-508 as discussed above and is able to be processed by system 10 as "No Pain". In this example, the value of the likelihood field is set to "actual" and does not appear in the resulting expected outcome name 500. Additionally, as the value in client field 504 is set to "Patient", this value also does not appear in the resulting expected outcome name. While the data values in fields 504 and 508 do not appear, these values exist as underlying parameters and during operation, system 10 is able to decompose expected outcome name 500 and utilize the values in fields 502-508.

Figure 5D:
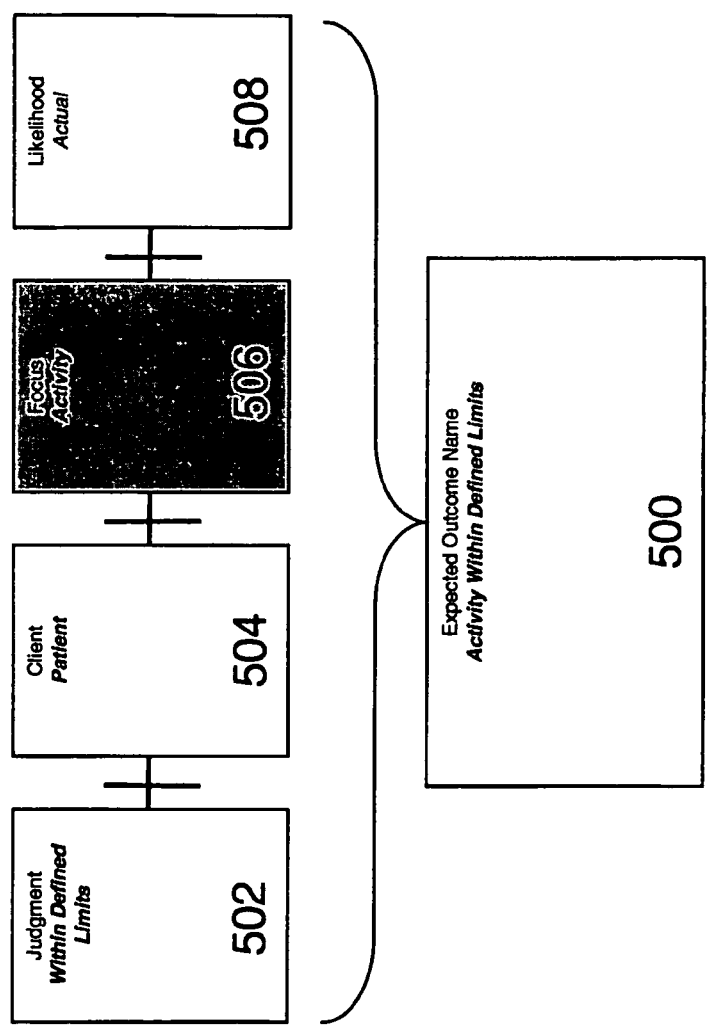

FIG. 5D is a further exemplary structure of an expected outcome name 500 and its associated attribute terms. In the example shown in FIG. 5D, the value in the judgment term field 502 does not appear as the first term in the resulting expected outcome name generated by system 10. The value in judgment term field 502 is a prepositional phrase, such as, "within defined limits", system 10 automatically structures the resulting expected outcome name to have the value in judgment term field 502 follow the value in focus term field 506. Thus, the value in focus term field 506 is the first word or term in expected outcome name 500.

Figure 5E:
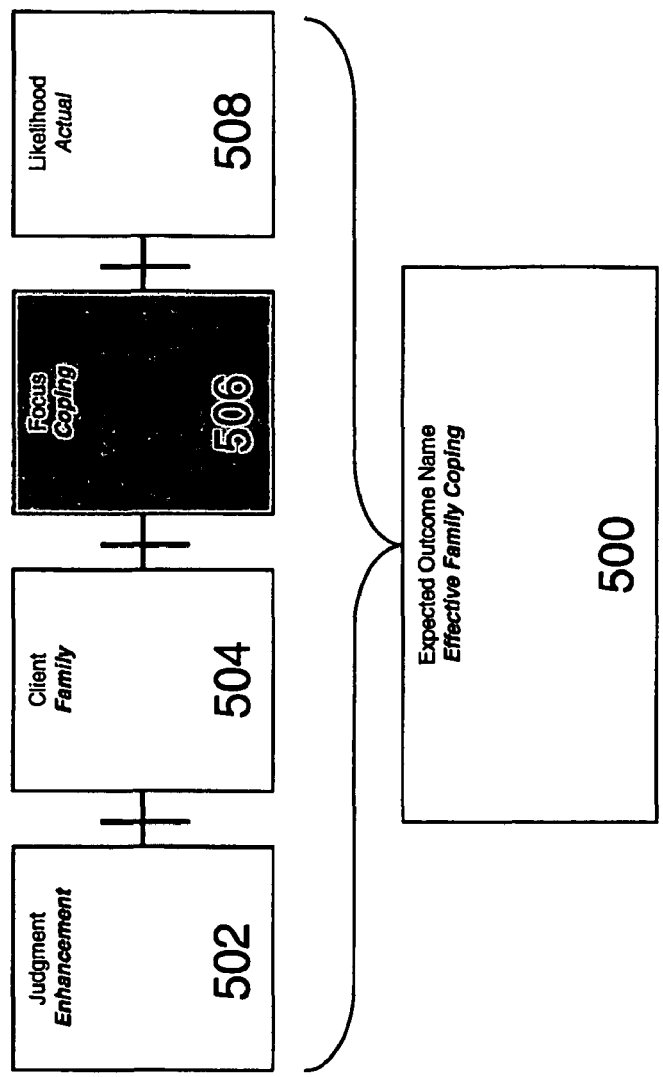

FIG. 5E shows another exemplary structure of an expected outcome name 500 and its associated attribute terms. Shown herein, the value in client term field 504 is not equal to "patient." In this instance, the value in client term field 504 is presented in the resulting expected outcome name 500 to further describe and/or qualify the value in focus term field 506. In FIG. 5E, client term field 504 has the value "family," and in expected outcome name 500, "family" precedes the focus term 506 for "coping." Additionally, the value in judgment term field 502 is set to "enhancement". This term is automatically translated by system 10 to a common term, "Effective" in the resulting expected outcome name further facilitating interoperability and understanding between different hospital information systems. Alternatively, in the instance when this exemplary expected outcome name data is received by a clinical information system (CIS), the CIS is able to computationally decompose expected outcome name data to derive the commonly understood meaning of judgment term as "Enhancement" of the particular focus activity for the particular client (e.g. patient or patient family).

Figure 5F:
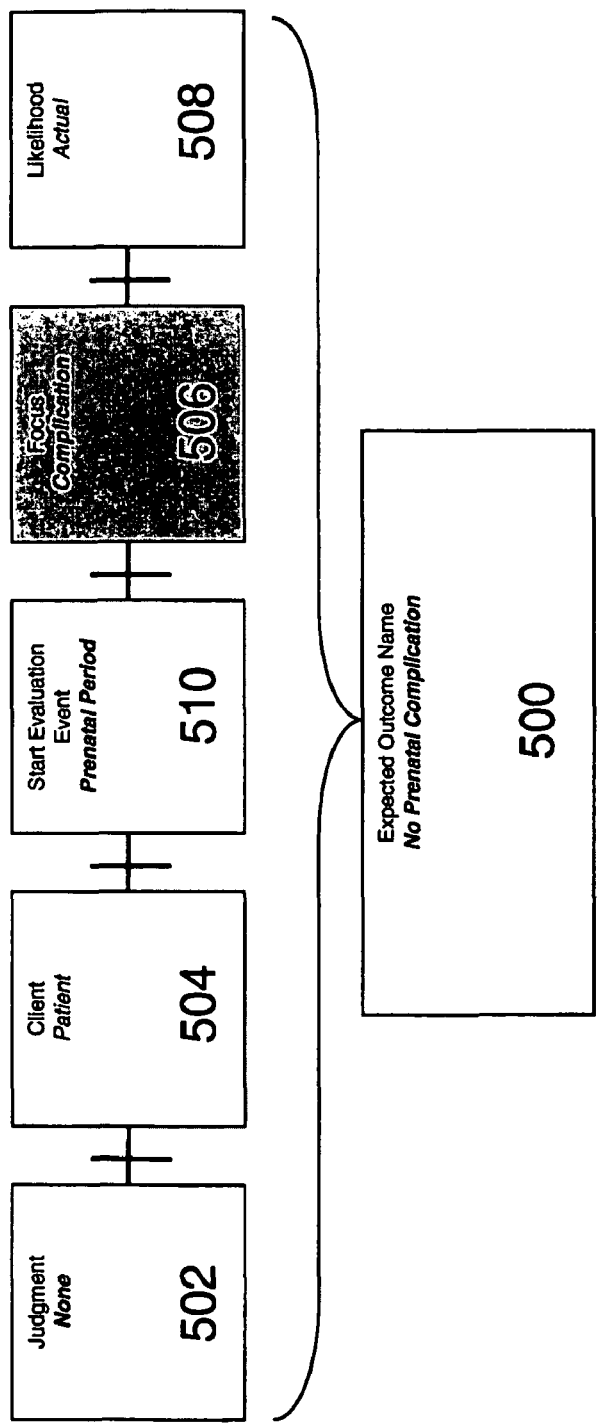

FIG. 5F is another exemplary structure of an expected outcome name 500 and its associated attribute terms. FIG. 5F illustrates the expandability provided by system 10 in creating and understanding the meaning of expected outcome name data. A further attribute field 510 defines data representing a start of evaluation for a particular event, "Start Evaluation Event". In the instance shown in FIG. 5F, the value in start evaluation event field 510 is set to "prenatal period". When start evaluation event 510 has a value, this value precedes the value for focus term 506 and judgment term 502 when formulating expected outcome name 500. This additional exemplary attribute field provides additional data values that are communicated to and used by applications throughout a healthcare information system.

Figure 6:
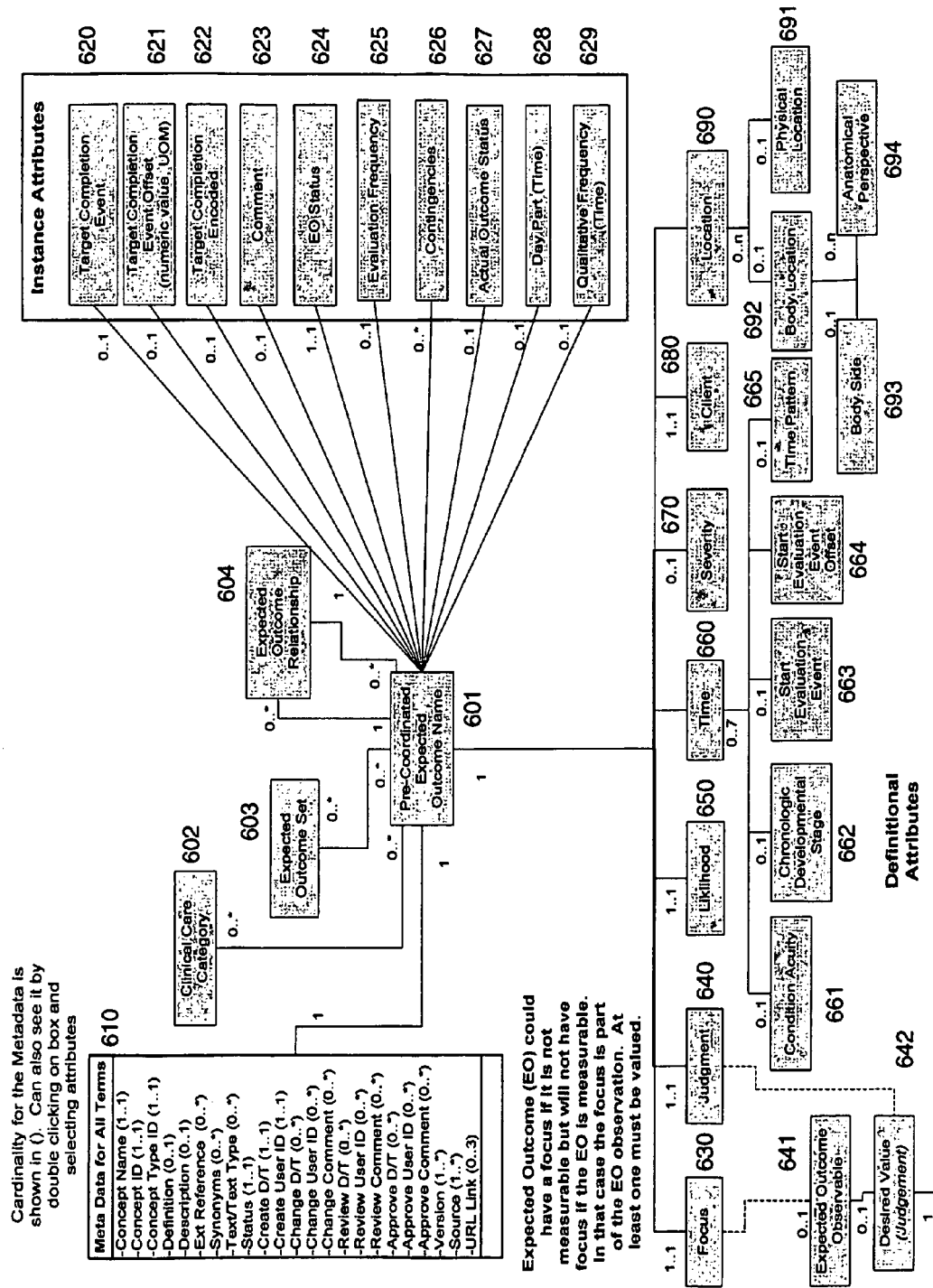
FIG. 6 is a block diagram showing the hierarchy and interrelationships of elements of an expected outcome according to invention principles.

An exemplary guideline for parameter value sequencing in an expected outcome name 601 is shown in FIG. 6. In relation to the parameter values, FIG. 6 depicts the hierarchy, as well as the interrelationships that exist within an expected outcome and its attributes or components. Data representing expected outcome name 601 that is stored and processed by system 10 includes definitional core attributes. Definitional core attribute data values are associated with a particular expected outcome definition instance and include focus term data 630, judgment term data 640, likelihood term data 650, and client term data 680. Focus term data 630 identifies the topic of attention (e.g., pain, knowledge deficit, or gas exchange). Judgment term data 640 describes the clinical opinion or determination about the actual or potential health problem or life process. This term may indicate positive (e.g., increase), or negative (e.g., impairment). Likelihood term data 650 describes the probable state of the topic of attention (e.g., actual or risk). Client term data 680 describes the target of care (e.g., patient, parent, or family). Additional attributes are also optionally defined by a user to provide further description of expected outcome name data 601.

Expected outcome name data further includes data representing a definitional modifier of a data value in a respective attribute data field. Definitional modifiers change the meaning of a base definition (e.g., adding negation or "family history of" to a medical problem name). In certain instances the value in judgment term field 640 also qualifies as a definitional modifier attribute since it is involved in changing the base definition of an expected outcome name. Expected outcome name data further includes data representing a definitional Qualifier of data in a particular attribute field. Definitional qualifier data values serve to further clarify and define a base definition of a value in a particular attribute data field.

A further attribute field associated with expected outcome name data 601 is a time attribute data field 660. The value of time attribute data field 660 is derived from values set in attribute sub-fields 661-665. The sub-fields that include values representing time attribute data include at least one condition acuity 661, chronologic developmental stage 662, start evaluation event 663, start evaluation event offset 664, and time pattern 665. Condition acuity data value 661 describes a determination derived from duration, and/or number of occurrences, and/or observations, and/or findings of a particular medical condition (e.g., acute or chronic). Chronologic developmental stage data value 662 describes human biological development, expressed as qualitative, age-related physical development stages (e.g., adolescence). Start evaluation event data value 663 and start evaluation event offset data value 664 are linked to one another. Both Start evaluation event data value 663 and start evaluation event offset data value 664 are used in determining when a user responsible for providing healthcare to a patient begins to evaluate a particular patient expected outcome. Start evaluation event data value 663 describes something that could or does take place or a situation having certain characteristics (e.g., admission or transfer), that indicates an expected outcome should be active. Start evaluation event data value includes occurrence data which indicates when to begin evaluating the expected outcome (e.g., outcome assignment, transfer from ICU, discontinuation of mechanical ventilation). Start evaluation event offset 664 is used to characterize the amount of time after the start evaluation event 663 has been initiated in order to calculate the actual date/time when the expected outcome becomes active, or when evaluation of the expected outcome begins (e.g., 0=immediately, 2 hours, 1 day). Time attribute data value 660 further includes a time pattern data value 665 which characterizes whether the related event occurs in an uninterrupted fashion (e.g., continuous, intermittent).

Expected outcome name data 601 further includes a Severity attribute data field 670 including a data value identifies a subjective measure of the relative, and non-quantitative, degree of the medical problem (e.g., mild, moderate, severe) valued in focus data field 630.

Location attribute data field 690 of expected outcome name data 601 includes data identifying a setting where an event, entity or process occurs or is located. However, the data value in location data field 690, similar to the data value in time data field 660, is derived from values set in attribute sub-fields 661-665. The sub-fields that include values representing time attribute data include at least one physical location data field 691 and body location data field 692. Data value in physical location data field 691 identifies a particular potion of space having substance or material existence (e.g., workplace). Data value in body location data field 692 identifies a bodily system, structure, region, or any component parts thereof Body location 692 is further characterized by attributes data fields for body side 693 and anatomical perspective 694. A value in body side data field 693 describes the side(s) of the body identified by location with respect to a center (e.g., left, right, bilateral). A value in anatomical perspective data field 694 describes a location in relation to sagittal, coronal, oblique, and transverse plans of the body (e.g., anterior, posterior, inferior). These attributes advantageously provide patient specific information that is utilized by a clinical application for generating a request for healthcare to be provisioned by a worker or for use in updating a task schedule of a healthcare professional to improve a level of patient care, for example.

Further attribute data fields 641, 642 and 643 include data values that further describe expected outcome name data 601. Expected outcome observable data 641 includes a data value describing a finding that is used to evaluate the actual outcome of the activity defined in focus data field 630 (e.g., Respiratory rate, O2 Saturation). Desired value data field 642 includes a data value that describes the result of a finding that is used to evaluate the actual outcome as defined by the data value in judgment data field 640 (e.g., Respiratory rate<24). Desired value UOM data field 643 includes a data value identifying a unit of measurement used to evaluate the actual outcome (e.g., per minute, percent, pounds, centimeters). The value in data field 643 is linked to and further defines the data value in desired value data field 642.

Expected outcome name data 601 further includes Clinical care category data field 602 which includes a data value identifying a category for grouping similar expected outcomes. This data value is used by a clinical application to visually organize the components of expected outcome name data on a user interface when presenting expected outcome name data to a healthcare provider.

Expected outcome set data field 603 is associated with expected outcome name data 601 and represents selectively configurable group of similar expected outcomes. Data values in expected outcome set data field 603 are used by system 10 during a search for and assignment of expected outcomes. For example, Dressing and Grooming Self Outcome Set
    Effective Ability to Comb Hair.
    Effective Ability to Wash Face.
    Effective Ability to Brush Teeth.
    Effective Ability to Clothe Upper Body.
    Effective Ability to Clothe Lower Body.
    Effective Ability to Secure Shoes.

Expected outcome name data 601 also includes an attribute identifying an instance when two or more expected outcomes are connected or associated, and information regarding how the behavior of one impacts the behavior of another different expected outcome. Data values identifying relationships between outcomes is set in expected outcome relationship data field 604. If a value appears in field 604, the value represents two types of relationships. A first data value is defined as "As Evidenced By," which is characterized by several measurable expected outcomes collectively used to determine the status of a single expected outcome. For example, adequate cardiac output may be evidenced by Clear breath sounds,
    No peripheral edema,
    Urine output greater than or equal to 30 milliliters/hour,
    No mental status changes A second data value is defined as an "Incremental Relationship," which identifies a progressive sequence of expected outcomes, such that the completion of one determines the onset of another expected outcome. For example, Ambulate 25 feet in hall by post-op day three.
    Dangle on edge of bed Post-op evening after surgery.
    Ambulate in room to door Post-operative day 1.
    Ambulate in hall 10 feet Post-operative day 2.

Further attribute data field used to characterize and describe expected outcome name data 601 include patient instance attribute data fields 620-629. Data values set in fields 620-629 are data values that have meaning in the context of a specific patient. The data values in fields 620-629 are included in an expected outcome models to direct operation of the user interface where data is collected by a healthcare professional. Patient instance attributes include Status data field 624 including a data value identifying a state documented at a point in time for the overall expected outcome (e.g., active, inactive, erroneous, and complete). Patient instance attributes further include status data field 627 having a data value describing a state documented at a point in time for the patient's actual status in meeting/completing the expected outcome (e.g., met, not met, progressing, improved, stabilized, deteriorated). Qualitative frequency data field 629 includes a data value identifying a subjective, and not quantitative, report of occurrences of events or activities within a given period of time (e.g., always, frequent, occasional, rarely). Day part data field 628 includes a data value identifying a part of the day (e.g., morning, afternoon) for any event or activity associated with an expected outcome. Comment data 623 includes data entered by a clinician to further describe the expected outcome for a particular patient.

Additional patient instance attribute data fields include a Target event completion data field 620. Target completion data for the expected outcome is defined as the anticipated point in time when the expected outcome is expected to be achieved (e.g., 1 day after assigned, 4 hours post admission, or by discharge). Data identifying a target completion point for a particular activity is set in field 620. In exemplary operation, in response to a clinical application receiving expected outcome name data including a value set in target event completion data field 620 and data value in status data field 627 indicating event is "not complete", clinical application generates an alert posts the alert message to a clinician's worklist notifying the clinician. The target completion event data field 620 alternatively includes data identifying an event called target completion event along with a numeric value with an associated unit of measure called target completion event offset 621. Target completion event 620 is an event used to determine the point in time an expected outcome target completion calculation should start (e.g., outcome assignment, expected outcome start event, admission, transfer, and discharge). Target completion event offset 621 includes a data value that describes the amount of time after the target completion event, and is used to calculate the actual date/time when the outcome should be complete. Data value in field 621 includes a unit of measure (e.g., 4 hours, 2 days, or 0). In exemplary operation, a clinical application receiving expected outcome name data include attribute data values in field 620 and 621 automatically translates data values in fields 620 and 621 into an actual date/time for a particular trigger event. Two examples using start evaluation event 662 and target completion, derived from target completion event 620 and target completion event offset 621, are shown below:

1. A patient is admitted with impaired gas exchange.
    Problem: Gas Exchange Impairment
    Expected Outcome: Within 2 days of admission, achieve adequate gas exchange without mechanical ventilation.
    Admission Date and Time: Dec. 12, 2006 1000
    Mechanical Ventilation Discontinuation: Dec. 12, 2006 1400
    Evaluation Event: Mechanical Ventilation Discontinuation
    Start Evaluation Event Offset: 0 hours
    Start Evaluation: Dec. 12, 2006 1400
    Target Completion Event: Admission
    Target Completion Event Offset: 2 days
Target Completion: Dec. 14, 2006 1000
2. A patient is admitted with impaired gas exchange.
    Problem: Gas Exchange Impairment
    Expected Outcome: Within 2 days of extubation, achieve adequate gas exchange.

Admission Date and Time: Dec. 12, 2006 1000
Mechanical Ventilation Discontinuation: Dec. 12, 2006 1400
Start Evaluation Event: Mechanical Ventilation Discontinuation
Start Evaluation Event Offset: 0 hours
Start Evaluation: Dec. 12, 2006 1400
Target Completion Event: Mechanical Ventilation Discontinuation
Target Completion Event Offset: 2 days
Target Completion: Dec. 14, 2006 1400

Target completion encoded data field 622 includes a data value that identifies a less structured or inexact point in time by which to achieve the expected outcome (e.g., after 3 treatments, by discharge, 6 hours post-op). No calculation of date/time is necessary, as this data is meant to provide information to clinicians for example, by automatically updating a monitoring schedule at a nursing station of a particular healthcare unit in a hospital.

Evaluation frequency data field 625 includes data values indicating how often a clinician is to evaluate progress in meeting the outcome (e.g., daily, every shift, and every week). Specific times may be associated with the time intervals.

Contingencies attribute data field 626 includes a data value identifying whether the expected outcome is dependent on the completion of another expected outcome.

Metadata attributes 610 are common concepts in the model. They provide additional information to describe the concept. Concept name provides a meaningful, unambiguous text string to represent a concept. The concept name needs to be individual within concept types.

Concept ID is a name used by applications for processing. An example of a concept ID for the unit of measure concept minutes is MIN. Applications recognize and correctly process minutes because the applications recognize the concept ID MIN.

Concept type defines the term type for a specific term. An individual term may be associated with more than one term type. For example, a term with the name WBC may operate as a service as well as an observation.

Description provides text describing or defining a concept.

External references are mechanisms used to associated external terminology and interface identifiers to concepts, as well as drive application logic. An external reference name is the name by which an entity, or other system, industry-standard terminology source, or content source, recognizes the concept.

Synonyms provide multiple names to be defined for one concept. This facilitates searching for a concept. A synonym is not used as the display name.

Text/TextType is text that may be any value appropriate in relationship to the text role code. The term text entity contains additional text about a specific concept and concept type.

Status indicates whether the concept is active or inactive.

Create D/T provides the date and time the concept was created.

Create user provides the user identifier or program of the concept creator.

Change D/T provides the date and time the term was most recently changed.

Change User ID provides the user identifier or program that last changed the concept.

Change Comment provides free text comments related to the revision.

Review D/T provides the date and time the term was reviewed.

Review User ID provides the user identifier of the user who last reviewed the concept.

Review Comment provides free text related to the review of this concept definition.

Approve D/T provides the date and time the concept was approved.

Approve User ID provides the user identifier of the user who approved the concept.

Approve Comment provides free text related to the concept approval.

Version provides a specific identifier for the concept version.

Source provides the source of concept description/definition.

URL Link provides a reference or navigation that automatically brings the referred information to the user when the navigation element is selected by the user.

Figure 7:
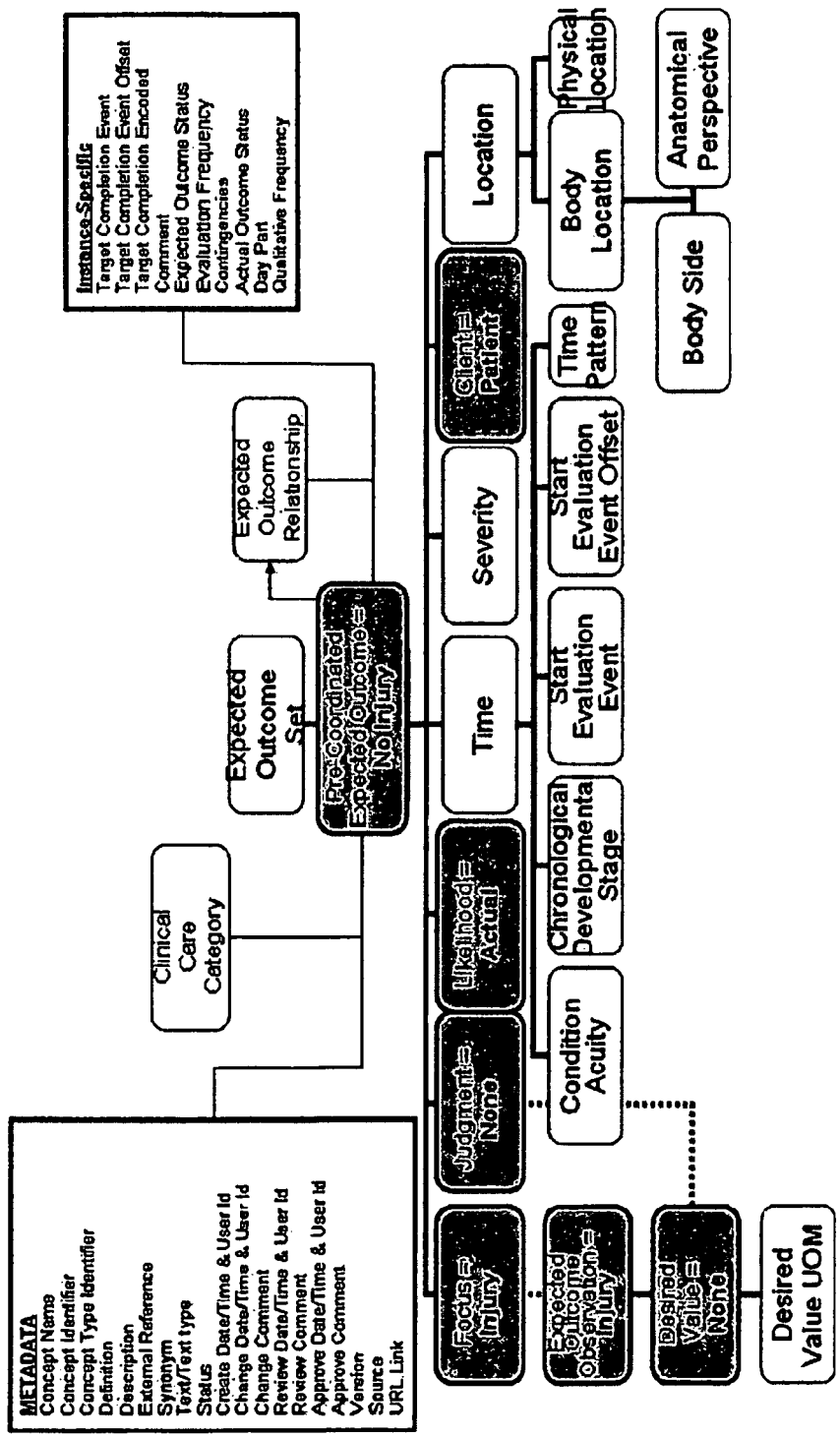
FIG. 7 is a block diagram showing one example of an expected outcome name according to invention principles.
Figure 8:
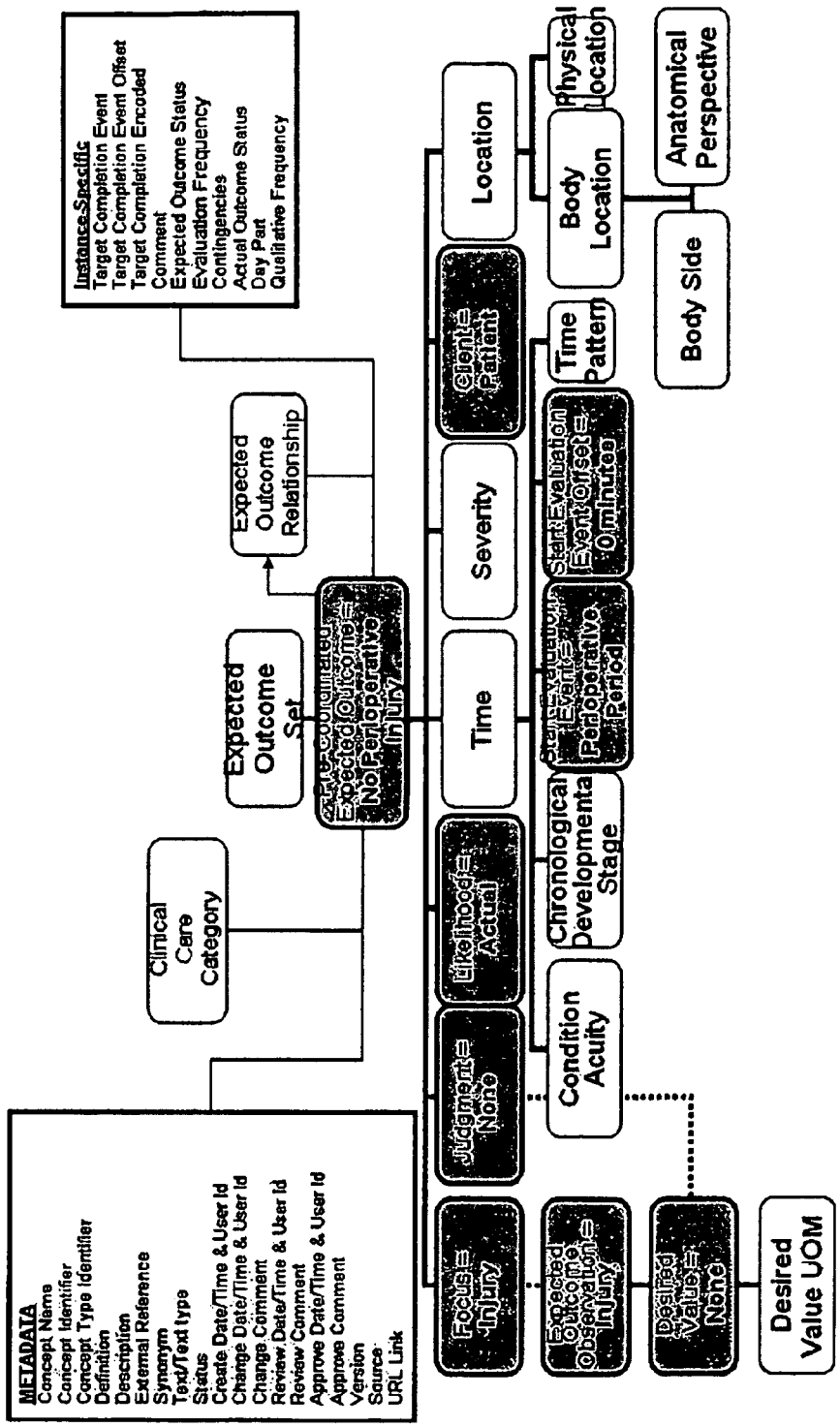
FIG. 8 is a block diagram showing a second example of an expected outcome name according to invention principles.

Two examples of how the expected outcome definition model core attributes may be valued to create an expected outcome definition instance are shown in FIGS. 7 and 8. The core attributes (focus term, judgment term, likelihood term and client term) that are a part of the fundamental definition of the expected outcome instance have been valued. With respect to FIG. 7, the focus term is valued as "Focus=Injury", the judgment term is valued as "Judgment=None", the likelihood term is valued as "Likelihood=Actual" and the client term is valued as "Client=Patient". Therefore, according to the predetermined naming rules discussed above with respect to FIGS. 5A-5F, the resulting expected outcome name is "No Injury". Referring now to FIG. 8, the core attribute values described with respect to FIG. 7 are the same. However, an additional attribute value, the start evaluation event attribute, is valued. In FIG. 8, the start evaluation event attribute is valued as "Start Event Evaluation=Perioperative Period". Thus, the expected outcome name defined by the model shown in FIG. 8 is "No Perioperative Injury". The differences between FIGS. 7 and 8 stem from the expected outcome name in FIG. 8 including a data value in an attribute data field, the start evaluation event being set as "perioperative", that is not present in the model shown in FIG. 7. Thus, it is demonstrated that simply changing the value of one core attribute (or adding a value to a further attribute data field) results in the meaning of the expected outcome definition instance to be changed.

Attribute properties are properties that further describe expected outcome attributes for use in particular clinical applications. For example, attribute data fields 620-694 in FIG. 6 each include at least one attribute property data field associated therewith. It should be noted that, any attribute data field associated with expected outcome name data may include at least one attribute property data field. Attribute property data fields are associated with respective clinical applications within a healthcare enterprise and data values in respective attribute property data fields are selectively useable by clinical applications directing the manner in which the clinical application handles and/or uses data in attribute data field with which attribute property data is associated. An individual clinical application that uses the expected outcome model of system 10 uses its own individual attribute properties to account for behavioral differences and constraints within a particular clinical application since each clinical application has its own business and user interface characteristics. An individual attribute property defines some application behavior, either for vocabulary authoring or the clinical application itself. Table 1 illustrates exemplary attribute properties and that property's appropriate default setting recommendation. An individual attribute property is used based on clinical application requirements.

TABLE 1

Attribute Property Data Values

| Short Name | Long Name | Definition |
|---|---|---|
| Dup Check | Duplicate Checking | This duplicate check indicator defines whether the value for this Parameter are included in clinical duplicate checking. If set to "Yes", this Parameter is used to check for duplicates when the expected outcome is added to the patient and when the expected outcome is added/revised in the vocabulary server and a default value is present. If the 'dup check' parameters are the same it is considered a duplicate. If ANY ONE of these 'dup check' parameters is different it will not be considered a duplicate. It is recommended that the default is set equal to "Yes" for any Parameter that is included in the definition instance model. |
| Req to Create | Required to Create Term | This indicator defines whether the model builder needs to enter a default value for this Parameter when an expected outcome is added or revised. Any Parameter that needs to have a default value to create the expected outcome should have this property set to Yes. |
| Allow Val Set | Allowable Value Set | The Allowable Value Set constrains the default values that may be entered for this Parameter when the expected outcome is added/revised in the vocabulary server, as well as in the clinical application. |
| Dflt Val | Default Value | The Default Value defines the Value that is automatically assigned for the Parameter. A Default Value can be entered if the data type of the Parameter is numeric, encoded or date offset. This value needs to be a member of the Allowable Value Set. It is beneficial to use this option if the default value is selected a high percentage of time. |
| UOM | Unit of Measure | The Unit of Measure is given a value if the Parameter accepts numeric or date offset values. The Unit of Measure is available for display with numeric values. It is also available for the clinical application to correctly set a default date/time based on the date offset value. |
| Decimal Places | Decimal Places | The Number of Decimal Places defines the number of digits to the right of the decimal that may be entered for the default value. This is valid for Parameters that accept numeric values. |
| Max No of Vals | Maximum Number of Values Allowed | The Maximum Number of Values Allowed determines the number of values that may be entered in the clinical application for a Parameter. The default value is set to 1 but can be changed to a number greater than 1 for those Parameters where it makes sense (e.g. Anatomical Perspective). |
| Req in Pt App | Required in Patient Application | Required in Patient Application indicates that the clinical application requires a value for the Parameter. There are 2 ways that the value can be set: the value can be provided when the definition is created for the expected outcome or the user clinician can provide a value. Any Parameter with a cardinality of 1:1 in the model should have this property to Yes. |
| Allow Free Text | Allow Free Text | Allow Free Text defines whether the patient application process allows a free text string to be entered for a Parameter that accepts encoded values. |
| Max Len | Maximum Length | Maximum Length determines the maximum number of characters that may be entered in the patient application for a Parameter that accepts free text value (Allow Free Text = Yes). |
| Set Mem Override | Set Member Override | Set Member Override defines whether the default value for this Parameter may be overridden when the related expected outcome term is a member of a Plan of Care. |
| Dsply in Pt App | Display in Patient Application | Display in Patient Application defines whether the default value for this Parameter is displayed in the patient application. This property is set to "No" if there is a Parameter value that does not provide value to the clinician at the point in time of expected outcome entry. For example, the Focus, Judgment, Likelihood and Client Parameters typically have a value assigned, and are not allowed to change when the expected outcome is assigned to a patient. There is no need to display the values to the user since they are represented in the expected outcome name. For example, a value may not be required for Chronological Development Stage for an expected outcome definition. The institution would like the clinician to enter a value for Chronological Development Stage. Set Display in Patient Application to Yes to display the prompt and the Allowable Value Set. The discrete values are available to the clinical application for secondary data use (e.g. Rules, Workflow) |

Figure 9:
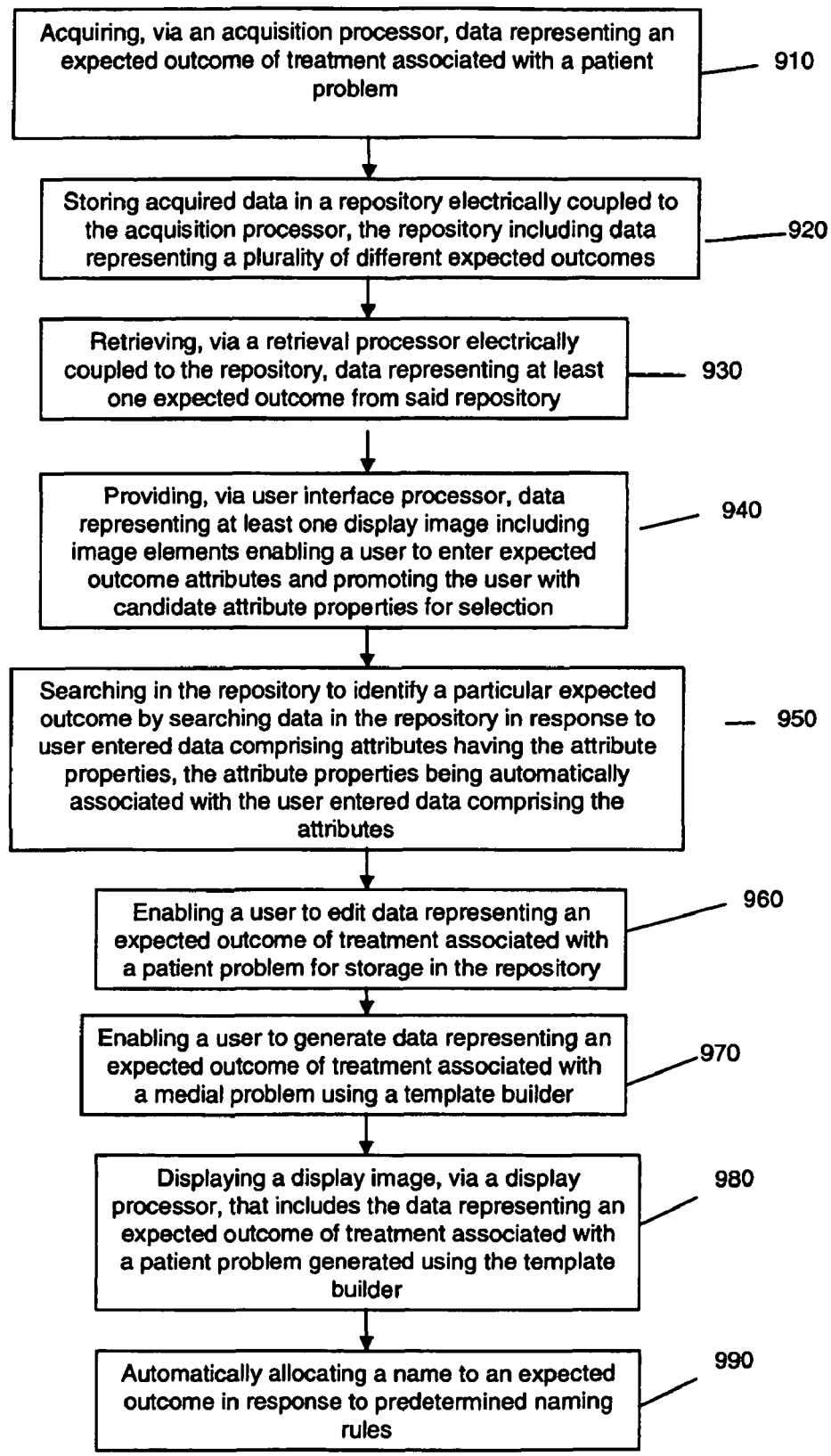
FIG. 9 is a flow diagram detailing system operation according to invention principles.

FIG. 9 is a flow diagram detailing operation of expected outcome data system 10 shown in FIG. 1. Expected outcome data system stores data representing a plurality of different expected outcomes of clinical care that are used in providing healthcare to a patient. In step 910, an acquisition processor acquires data representing an expected outcome of treatment associated with a medical problem. Acquisition processor further acquires data representing an expected outcome compatible with the attribute properties. Data acquired by acquisition processor in step 910 is also converted to be compatible with the attribute properties.

The acquired data is stored, as in step 920, in a repository. The repository is electrically coupled to the acquisition processor and includes data representing a plurality of different expected outcomes. An individual expected outcome has an expected outcome name and is characterized by expected outcome attributes. The expected outcome attributes include a focus term indicating a topic of an expected outcome, an expected outcome likelihood term indicating an assessment of likelihood of the associated corresponding expected outcome, and a client term indicating at least one target person for care. Expected outcome attributes also include at least one of (a) medical condition acuity data, (b) chronologic development stage of a medical condition, (c) an indication of a clinical event and (d) an indication of a time pattern associated with a medical condition, (e) data representing an indication of review action needed in treatment of a medical condition, (f) data representing an indication of approval action needed in treatment of a medical condition, and (g) a judgment term indicating a clinical opinion concerning an expected outcome. The clinical opinion in the judgment term indicates at least one of, (a) a positive, (b) a negative and (c) a neutral, status of an expected outcome.

An individual expected outcome attribute has a plurality of attribute properties determining how an expected outcome attribute is represented. The attribute properties associated with the attributes include a format attribute property indicating a format constraint of an expected outcome attribute, and a content attribute property indicating a content constraint of an expected outcome attribute. The format attribute property comprises at least one of, (a) maximum character length of an attribute, (b) a unit of measure of an attribute and (c) a number of decimal places an attribute has. The content attribute properties comprising at least two of, (a) an allowable value set of an attribute, (b) a default value of an attribute, (c) a maximum number of values allowed for an attribute and (d) an indication free text entry is allowed for user entry of data representing an attribute. The attribute properties further includes a processing attribute property comprising at least one of, (a) an indication an attribute is to be processed in performing a check for a duplicate medication and (b) an indication a default value is required for an attribute. Alternatively, the processing attribute properties comprises at least one of, (a) an indication an attribute is required for use by an executable clinical application and (b) an indication an attribute is displayed in a display image associated with said executable clinical application. In a further embodiment, the attribute properties include processing attribute properties comprising an indication an attribute value may be overridden.

The repository further associates an individual expected outcome of treatment associated with a medical problem with metadata attributes including at least one of, a problem identifier, external references and synonyms. Metadata attributes alternatively include data identifying who created, changed or reviewed expected outcome information.

A retrieval processor, electrically coupled to said repository, retrieves data representing at least one expected outcome from said repository in step 930. A user interface processor provides data representing at least one display image including image elements enabling a user to enter expected outcome attributes and for prompting the user with candidate attribute properties for selection in step 940. The at least one display image includes image elements for prompting the user with candidate attributes for selection and inclusion in expected outcome attributes. User interface processor alternatively provides data representing at least one display image enabling a user to enter at least one of genomic and proteomic data associated with a particular patient. In response thereto, system provides the user with candidate attribute properties for selection in response to the at least one of patient specific genomic and proteomic data.

In step 950, a data processor searches data in the repository to identify a particular expected outcome in response to user entered data comprising attributes having the attribute properties, the attribute properties being automatically associated with the user entered data comprising the attributes. The searching in step 950 further includes searching to identify at least one of, (a) a candidate plan of care, (b) a treatment and (c) a diagnosis, associated with a particular expected outcome by searching data in the repository in response to user entered data identifying expected outcome attributes having the attribute properties. Alternatively, the search step 950 includes searching data in the repository in response to patient-specific genomic and/or proteomic data to identify at least one of, (a) a candidate plan of care, (b) a treatment and (c) a diagnosis, associated with a particular patient problem by searching data in the repository in response to user entered data identifying patient problem attributes having the attribute properties.

An edit processor, in step 960, enables a user to edit data representing an expected outcome of treatment associated with a medical problem for storage in the repository. A template builder processor, in step 970, enables a user to generate data representing an expected outcome of treatment associated with a medical problem and a display processor generates data representing at least one display image including the data representing an expected outcome of treatment associated with a medical problem generated using the template builder in step 980. In step 990, a name processor automatically allocates a name to an expected outcome in response to predetermined naming rules.

Referring back to FIG. 1, a user of system 10 is able to selectively create and modify expected outcome name data for a particular expected patient outcome. A user selectively sets data values for any of the plurality of attribute data fields described in FIG. 6 and attribute property data values described in Table 1. System 10 also automatically acquires data representing expected outcome names for particular healthcare activities. The acquired expected outcome name data include terms that correspond to at least one attribute data field identifying a meaning of the term. Also included are data values for predetermined attribute data fields that are used to further describe the expected outcome. The system searches repository 20 for instances of terms and, if none are found automatically creates an expected outcome name record. The record created in repository 20 includes attribute data field associated with the received expected outcome data. The system automatically populates the attribute data field in the created record with corresponding attribute data associated with the acquired expected outcome data. Once stored, system 10 users can selectively modify data values stored in the record. Alternatively, users are able to add additional attribute fields and set data values for the added fields. These added fields are used by clinical application for driving operation of a particular application and/or identifying how data associated with the clinical application is to be presented to a user. Thus, system 10 advantageously enables consistent, model-driven application and user interface behavior associated with the collection, translation and interpretation of patient expected outcomes. The system includes a model structure including detailed attributes associated with patient expected outcomes and supplemental information associated with patient expected outcomes that is necessary to drive application behavior.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An expected outcome data system storing data representing a plurality of different expected outcomes of patient care and treatment for use in providing healthcare to a patient, comprising:

an acquisition processor for acquiring data representing an expected outcome of treatment associated with a medical problem, for storage in a repository;

at least one repository, electrically coupled to said acquisition processor, including data representing a plurality of different expected outcomes of treatment and an individual expected outcome of treatment has an expected outcome name and is characterized by expected outcome attributes and an individual expected outcome attribute has a plurality of attribute properties determining how an expected outcome attribute is represented, said expected outcome attributes including,
- a focus term indicating a topic of an expected outcome,
- an expected outcome likelihood term indicating an assessment of likelihood of the associated corresponding expected outcome, and
- a client term indicating at least one target person for care;

said attribute properties including,
- a format attribute property indicating a format constraint of said expected outcome attribute and determining formatting or presentation of said expected outcome attribute, and
- a content attribute property indicating a content constraint of said expected outcome attribute and determining modification of said expected outcome attribute; and a retrieval processor, electrically coupled to said repository, for retrieving data representing at least one expected outcome from said repository and communication of said expected outcome attributes to a destination system for processing data representing an expected outcome in response to said attribute properties.

2. A system according to claim 1, including
a user interface processor for providing data representing at least one display image including image elements enabling a user to enter expected outcome attributes and for prompting said user with candidate attribute properties for selection.

3. A system according to claim 2, wherein
said at least one display image includes image elements for prompting said user with candidate attributes for selection.

4. A system according to claim 1, wherein
said acquisition processor acquires data representing an expected outcome compatible with said attribute properties for storage in said repository.

5. A system according to claim 1, including
a data converter for converting data representing an expected outcome acquired by said acquisition processor to be compatible with said attribute properties for storage in said repository.

6. A system according to claim 1, including
a data processor for searching data in said repository to identify a particular expected outcome by searching data in said repository in response to user entered data comprising attributes having said attribute properties, said attribute properties being automatically associated with said user entered data comprising said attributes.

7. A system according to claim 6, wherein
said data processor searches data in said repository to identify at least one of, (a) a candidate plan of care, (b) a treatment and (c) a diagnosis, associated with a particular expected outcome by searching data in said repository in response to user entered data identifying expected outcome attributes having said attribute properties.

8. A system according to claim 1, wherein
said attribute properties include a format attribute property comprising at least one of, (a) maximum character length of an attribute, (b) a unit of measure of an attribute and (c) a number of decimal places an attribute has.

9. A system according to claim 1, wherein
said attribute properties include content attribute properties comprising at least two of, (a) an allowable value set of an attribute, (b) a default value of an attribute, (c) a maximum number of values allowed for an attribute and (d) an indication free text entry is allowed for user entry of data representing an attribute.

10. A system according to claim 1, wherein
said attribute properties include processing attribute properties comprising at least one of, (a) an indication an attribute is to be processed in performing a check for a duplicate expected outcome and (b) an indication a default value is required for an attribute.

11. A system according to claim 1, wherein
said attribute properties include processing attribute properties comprising at least one of, (a) an indication an attribute is required for use by an executable clinical application and (b) an indication an attribute is displayed in a display image associated with said executable clinical application.

12. A system according to claim 1, wherein
said attribute properties include processing attribute properties comprising an indication an attribute value may be overridden.

13. A system according to claim 1, wherein
said expected outcome attributes include medical condition acuity.

14. A system according to claim 1, wherein
said expected outcome attributes include at least one of, (a) chronologic development stage of a medical condition, (b) an indication of a clinical event and (c) an indication of a time pattern associated with a medical condition.

15. A system according to claim 1, wherein
said expected outcome attributes include an indication of review action needed in treatment of a medical condition.

16. A system according to claim 1, wherein
said expected outcome attributes include an indication of approval action needed in treatment of a medical condition.

17. A system according to claim 1, wherein
said data representing a plurality of different expected outcomes comprises data representing names of expected outcomes and
including a name processor for automatically allocating a name to an expected outcome in response to predetermined naming rules.

18. A system according to claim 1, wherein
said expected outcome attributes include a judgment term indicating a clinical opinion concerning an expected outcome.

19. A system according to claim 18, wherein
said clinical opinion indicates at least one of, (a) a positive, and (b) a negative status of an expected outcome.

20. A system according to claim 1, including
an edit processor enabling a user to edit data representing an expected outcome of treatment associated with a medical problem for storage in said repository.

21. A system according to claim 1, including
a template builder processor enabling a user to generate data representing an expected outcome of treatment associated with a medical problem.

22. A system according to claim 21, including
a display processor for generating data representing at least one display image including said data representing an expected outcome of treatment associated with a medical problem generated using said template builder.

23. A system according to claim 1, wherein
said repository associates an individual expected outcome of treatment associated with a medical problem with metadata attributes including at least one of, a problem identifier, external references and synonyms.

24. A system according to claim 1, wherein
said repository associates an individual expected outcome of treatment associated with a medical problem with metadata attributes including data identifying who created, changed or reviewed medical problem information.

25. A method for storing and retrieving expected outcome data representing a plurality of different expected outcomes of patient care and treatment for use in providing healthcare to a patient, comprising the activities of
acquiring data representing an expected outcome of treatment associated with a medical problem, for storage in a repository;
storing data representing a plurality of different expected outcomes of treatment and an individual expected outcome of treatment has an expected outcome name and is characterized by expected outcome attributes and an individual expected outcome attribute has a plurality of attribute properties determining how an expected outcome attribute is represented,
said expected outcome attributes including,
a focus term indicating a topic of an expected outcome,
an expected outcome likelihood term indicating an assessment of likelihood of the associated corresponding expected outcome, and
a client term indicating at least one target person for care;
said attribute properties including,
a format attribute property indicating a format constraint of an expected outcome attribute and determining formatting or presentation of said expected outcome attribute and determining formatting or presentation of said expected outcome attribute, and
a content attribute property indicating a content constraint of said expected outcome attribute and determining modification of said expected outcome attribute and determining modification of said expected outcome attribute; and
retrieving data representing at least one expected outcome; and
communicating said expected outcome attributes to a destination system for processing data representing an expected outcome in response to said attribute properties.

* * * * *